US011123934B2

(12) United States Patent
Rajala et al.

(10) Patent No.: US 11,123,934 B2
(45) Date of Patent: Sep. 21, 2021

(54) METHOD OF FORMING A COMPOSITE WEB UTILIZING A ROTARY BONDING SYSTEM WITH AN ANVIL PATTERN

(71) Applicant: Kimberly-Clark Worldwide, Inc., Neenah, WI (US)

(72) Inventors: Gregory John Rajala, Neenah, WI (US); Jason Kyle Sieck, Neenah, WI (US); Kenneth John Wagner, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 264 days.

(21) Appl. No.: 16/344,587

(22) PCT Filed: Oct. 31, 2016

(86) PCT No.: PCT/US2016/059643
§ 371 (c)(1),
(2) Date: Apr. 24, 2019

(87) PCT Pub. No.: WO2018/080530
PCT Pub. Date: May 3, 2018

(65) Prior Publication Data
US 2019/0240920 A1 Aug. 8, 2019

(51) Int. Cl.
*B32B 37/00* (2006.01)
*B29C 65/00* (2006.01)
(Continued)

(52) U.S. Cl.
CPC .......... *B29C 66/8362* (2013.01); *A61F 13/15* (2013.01); *A61F 13/15699* (2013.01);
(Continued)

(58) Field of Classification Search
USPC .......... 156/73.1
See application file for complete search history.

(56) References Cited

U.S. PATENT DOCUMENTS 5,552,013 A 9/1996 Ehlert et al.
5,643,396 A 7/1997 Rajala et al.
(Continued)

FOREIGN PATENT DOCUMENTS

CN 106029022 A 10/2016
JP 4999372 B2 8/2012
(Continued)

*Primary Examiner* — James D Sells
(74) *Attorney, Agent, or Firm* — Kimberly-Clark Worldwide, Inc.

(57) ABSTRACT

A method of bonding a first web of material to a second web of material to form a composite material is disclosed herein. First, a first web of material and a second web of material moving in a machine direction is provided. The webs of material pass over a first energy application device extending transverse in the cross-machine direction. The first energy application device includes a primary bonding pattern and a secondary bonding pattern. The primary bonding pattern in combination with the secondary bonding pattern extends continuously across the first energy application device in the cross-machine direction. In addition, a second energy application device is provided. The second energy application device is moved in the cross-machine direction, and thereby extending the second energy application device over the first energy application device and operating the first and second energy application devices in combination to bond a composite web.

26 Claims, 5 Drawing Sheets

(51) Int. Cl.

| | |
|---|---|
| ***A61F 13/15*** | (2006.01) |
| ***B29C 65/08*** | (2006.01) |
| ***B32B 5/26*** | (2006.01) |
| ***B32B 5/02*** | (2006.01) |
| *B29L 31/48* | (2006.01) |

(52) U.S. Cl.

CPC ...... *A61F 13/15739* (2013.01); *B29C 65/085* (2013.01); *B29C 66/0326* (2013.01); *B29C 66/1122* (2013.01); *B29C 66/21* (2013.01); *B29C 66/223* (2013.01); *B29C 66/232* (2013.01); *B29C 66/43* (2013.01); *B29C 66/7294* (2013.01); *B29C 66/81433* (2013.01); *B29C 66/81435* (2013.01); *B32B 5/02* (2013.01); *B32B 5/022* (2013.01); *B32B 5/26* (2013.01); *A61F 2013/15869* (2013.01); *B29L 2031/4878* (2013.01); *B32B 2555/02* (2013.01)

(56) References Cited

U.S. PATENT DOCUMENTS

| | | | |
|---|---|---|---|
| 5,667,608 A | 9/1997 | Rajala et al. | |
| 5,817,199 A | 10/1998 | Brennecke et al. | |
| 6,165,298 A | 12/2000 | Samida et al. | |
| 6,287,403 B1 | 9/2001 | Couillard et al. | |
| 6,517,650 B2 | 2/2003 | Couillard et al. | |
| 6,537,401 B2 | 3/2003 | Couillard et al. | |
| 6,540,854 B2 | 4/2003 | Couillard et al. | |
| 6,713,159 B1 | 3/2004 | Blenke et al. | |
| 6,939,335 B2 | 9/2005 | Franke et al. | |
| 7,056,313 B2 | 6/2006 | Franke et al. | |
| 7,056,404 B2 | 6/2006 | McFall et al. | |
| 7,060,142 B2 | 6/2006 | Yamamoto | |
| 7,108,759 B2 * | 9/2006 | You .................. | A61F 13/15593 156/73.1 |
| 8,197,458 B2 | 6/2012 | Bäck | |
| 8,449,519 B2 | 5/2013 | Een et al. | |
| 9,254,585 B2 | 2/2016 | Schmitz | |
| 9,295,593 B2 | 3/2016 | Van Malderen | |
| 2002/0062902 A1 | 5/2002 | Couillard et al. | |
| 2002/0148548 A1 | 10/2002 | Murie et al. | |
| 2006/0149209 A1 | 7/2006 | Malchow et al. | |
| 2007/0137762 A1 | 6/2007 | Topolkaraev et al. | |
| 2010/0040903 A1 | 2/2010 | Kalt et al. | |

FOREIGN PATENT DOCUMENTS

| | | | |
|---|---|---|---|
| JP | 2014233624 | A | 12/2014 |
| WO | 08041639 | A1 | 4/2008 |
| WO | 10068150 | A1 | 6/2010 |
| WO | 136167172 | A1 | 11/2013 |

* cited by examiner

METHOD OF FORMING A COMPOSITE WEB UTILIZING A ROTARY BONDING SYSTEM WITH AN ANVIL PATTERN

BACKGROUND OF THE DISCLOSURE

Thermal bonding using ultrasonics to form nonwovens and provide embossing patterns is well known for those skilled in the art. For example, ultrasonic bonding has been utilized to make disposable type garments such as diapers, training pants, feminine care products, incontinence garments, and in particular for forming of side seams for these types of articles.

Design of the absorbent articles requires certain physical requirements for these bond to perform as intended. It has been shown that a pattern of rectangular shaped bars, where the bars are oriented perpendicular to the edge of the product, yields the highest bond strength and greatest percent elongation at failure versus e.g., a dot pattern of equivalent surface area, resulting in a product that works and functions as intended.

However, a pattern of bars oriented perpendicular to the edge of the product poses certain operational problems for rotary bonding systems. For example, as an ultrasonic horn presses against an anvil and moves parallel to the anvil axis, the contact area between ultrasonic horn and anvil varies as a function of the horn's position along the anvil due to the raised bonding pattern protruding from the anvil's surface. Therefore, a pattern comprised only of a series of bars oriented perpendicular to the anvil axis means that the horn experiences interruptions in contact area as it rolls along the anvil. The interruptions in contact between horn and anvil can excite structural resonances in the anvil, the anvil support, and the horn support structures resulting in bond strength variability and ultrasonic generator overloads. This problem ultimately leads to waste and loss of productivity.

Therefore, there is a need to develop an ultrasonic bonding system and method that provides an ability to provide a bonded composite web that includes the requisite strength in bonds, while eliminating waste caused by instability within the bonding system.

SUMMARY OF THE DISCLOSURE

In one embodiment, a method of bonding a first web of material to a second web of material to form a composite material is disclosed herein. First, a first web of material and a second web of material moving in a machine direction is provided. The webs of material pass over a first energy application device extending transverse in the cross-machine direction. The first energy application device includes a primary bonding pattern and a secondary bonding pattern. The primary bonding pattern in combination with the secondary bonding pattern extends continuously across the first energy application device in the cross-machine direction. In addition, a second energy application device is provided. The second energy application device is moved in the cross-machine direction, and thereby extending the second energy application device over the first energy application device and operating the first and second energy application devices in combination. Energy is thereby applied to the first web of material and the second web of material at a line moving progressively across the first web of material and a second web of material to bond the first web of material to the second web of material and form a composite material.

In one embodiment, a method of bonding a first web of material to a second web of material to form a composite material is disclosed herein. First, a first web of material and a second web of material moving in a machine direction is provided. The webs of material pass over a first energy application device extending transverse in the cross-machine direction. The first energy application device includes a primary bonding pattern and a secondary bonding pattern. In addition, a second energy application device is provided. The second energy application device is moved in the cross-machine direction, and thereby extending the second energy application device over the first energy application device and operating the first and second energy application devices in combination. Energy is thereby applied to the first web of material and the second web of material at a line moving progressively across the first web of material and a second web of material to bond the first web of material to the second web of material and form a composite material. During operation, the primary bonding pattern provides non-continuous contact between the first energy application device and the second energy application device in the cross-machine direction and the secondary bonding pattern provides continuous contact between the first energy application device and the second energy application device in the cross-machine direction.

In exemplary embodiments, the first energy application device comprises an anvil the second energy application device comprises a rotary ultrasonic horn. During operation, energy may be applied to the first web of material and the second web of material only through the primary bonding pattern.

The secondary bonding pattern provides support for the secondary energy application device when operating the first and second energy applications in combination. In this embodiment, the secondary bonding pattern does not provide energy to the first web of material and the second web of material.

In some embodiments, the secondary bonding pattern is not continuous in the cross-machine direction preventing severing of the composite during bonding. This allows for maintaining the web for further processing of the composite material after bonding the first web of material to the second web of material.

In another exemplary embodiment, the primary bonding pattern comprises at least one row of discreet bars extending in the machine direction, wherein the discreet bars are spaced apart in the cross-machine direction. In this embodiment, the secondary bonding pattern provides support for the second energy application device where the discreet bars are spaced apart. Desirably, the primary bonding pattern comprises two rows of discreet bars extending in the machine direction wherein the discreet bars are spaced apart in the cross-machine direction.

The secondary bonding pattern may have a number of different designs. For example, the secondary bonding pattern comprises discreet bars extending at an angle to the machine direction. In another example, the secondary bonding pattern comprises a series of circular elements extending across the first energy application device in the cross-machine direction.

BRIEF DESCRIPTION OF THE DRAWINGS

A full and enabling disclosure thereof, directed to one of ordinary skill in the art, is set forth more particularly in the remainder of the specification, which makes reference to the appended figures in which.

Figure 1:
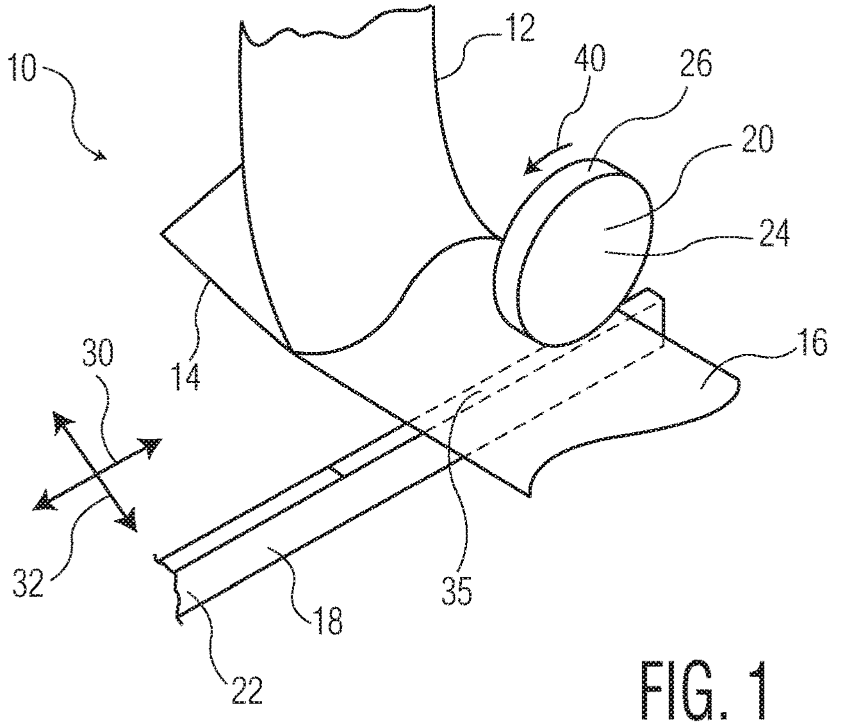
FIG. 1 is a top, side perspective view of an exemplary embodiment of an ultrasonic bonding system for use to bond together two materials illustrating an anvil and rotary ultrasonic horn.

Repeat use of reference characters in the present specification and drawings is intended to represent the same or analogous features or elements of the disclosure.

DETAILED DESCRIPTION OF THE DISCLOSURE

FIG. 1 illustrates one embodiment of a bonding system 10 described herein. The bonding system 10 may be comprised of any device by which the transfer of thermal energy is sufficient to weld the material together, such as electrical resistance devices such as continuously heated or intermittently heated impulse type devices, pressure or induction heated components. Desirably, the thermal energy source is provided by the use of ultrasonic energy.

The ultrasonic bonding system 10 may be used to make disposable type garments such as diapers, training pants, feminine care products, incontinence garments, and the like, and includes methods for joining two superposed composite webs by producing ultrasonic bonds at spaced apart locations extending across the webs in directions transverse (cross-machine direction) to the direction of travel of the webs in the processing apparatus (machine direction). Desirably, the production of disposable type garments in a continuous combined web, where the garments in the web extend transverse to the web, with the waist portions of the garments extending along the machine direction of the web, and the front and back portions of the garments being on opposing sides of the web. In the embodiments illustrated, the bonds join the two webs of material at locations generally corresponding to the ultimate locations of side seams in the finished garments.

In forming such bonds using known technology, it is difficult to obtain uniform application of thermal energy across the entire width of the web, whereby the bonds may exhibit less than the desired uniformity. The apparatus and methods disclosed herein provide a novel approach to achieving predictably uniform bond strength.

As seen in FIG. 1, an ultrasonic bonding system 10 to bond a first web of material 12 to a second web of material 14 and form a composite material 16 is disclosed herein. First, a first web of material 12 and a second web of material 14 are provided moving in a machine direction 32. The webs of material 12, 14 pass over a first energy application device 18 extending in the cross-machine direction 30. In addition, a second energy application device 20 is provided. The second energy application device 20 is moved in the cross-machine direction 30 by rotating in direction 40, and thereby extending the second energy application device 20 over the first energy application device 18 and operating the first and second energy application devices 18, 20 in combination. Energy, preferably ultrasonic energy, is thereby applied to the first web of material 12 and the second web of material 14 at a line moving progressively across the first web of material 12 and a second web of material 14 to bond the first web of material to the second web of material and form a composite material 16.

In one exemplary an ultrasonic bonding system 10, the first energy application device 18 is an anvil 22, and the second energy application device 20 comprises the ultrasonic horn 24. In alternative embodiments, the first energy application device 18 is an ultrasonic horn 24, and the second energy application device 20 comprises an anvil 22. The anvil 22 may comprise a metal bar extending in the cross-machine direction 30.

The ultrasonic horn 24 is preferably mounted to extend over the anvil 22, to apply downward pressure on webs of material 12, 14 while on the anvil 22, thereby to apply ultrasonic energy to the webs of material 12, 14 while being extended over the anvil 22, and to subsequently withdraw from over the anvil 22. The ultrasonic horn 24 may be mounted to traverse an energy application path 35 over the anvil and webs of material 12, 14 on the anvil 22, the energy application path 35 being oriented in a cross-machine direction 30 across the webs of material 12, 14. The ultrasonic bonding system 10 preferably further includes a method for simultaneously applying both pressure and ultrasonic energy through the ultrasonic horn 24, to the webs of material 12, 14 disposed on the anvil, thereby pressure bonding the webs 12, 14 of material while the ultrasonic horn 24 is so passing over the webs of material 12, 14 on the anvil 22.

Preferably, as shown in FIG. 1, the ultrasonic horn 24 comprises a wheel 26, thus a rotary ultrasonic horn, mounted for rotation about a second axis, to thereby apply ultrasonic energy to the webs of material 12, 14 moving across the webs of material in a cross-machine direction 30 as the ultrasonic horn 24 traverses the energy application path 35. The energy application path 35 may include an outgoing segment wherein the rotary ultrasonic horn 24 is extended over the anvil and an incoming segment wherein the rotary ultrasonic horn is withdrawn from over the anvil, the ultrasonic system further applies pressure through the rotary ultrasonic horn 24 to the webs of material 12, 14 as the ultrasonic horn 24 traverses the energy application path 35 to thereby apply pressure through the rotary ultrasonic horn 24 to the webs of material 12, 14 on one of the segments of the energy application path 35, preferably the outgoing segment, and to withhold the pressure on the other segments of the energy application path 35.

In some embodiments, the ultrasonic bonding system 10 may further comprise at least two ultrasonic horns mounted at different radial locations about the outer working surface of a drum, and corresponding at least two anvils, preferably rotary anvils, mounted for rotation with the drum and over respective ones of the at least two ultrasonic horns. Examples of such ultrasonic bonding systems can be found in U.S. Pat. No. 5,667,608 to Rajala et al., which is hereby incorporated by reference.

Typically, one of the energy application devices 20 has a generally smooth outer circumferential surface 26 while the other energy application device 18 includes a primary and secondary pattern 60, 62 of raised bonding protrusions corresponding in design and location to the bonding pattern reflected in FIGS. 3-7. In the embodiments shown, the anvil 22 includes the primary bonding pattern 60 and the secondary bonding pattern 62 extending from the anvil's base surface 64.

The individual protrusions extend from a base surface 64 on the first energy application device 18. The protrusions terminate at distal end surfaces which are responsible for creating the respective bond elements 54. Typically such protrusions can be, for example, up to approximately 0.10 inch in height, and up to about 0.06 inch in width. Height is defined as the dimension of the protrusion from the base circumferential surface of the roll to the distal tip, or land, which actually interfaces with e.g. the web material in which bonds are being formed.

The primary bonding pattern 60 and secondary bonding pattern 64, as well as the individual bonding elements 54, can be activated by a variety of methods including but not limited to applying pressure, thermal energy and pressure, or ultrasonic-frequency energy and pressure, to bond the two webs of material together. Desirably, when ultrasonic energy is employed, the e.g. anvil roll 20 is properly sized, as known in the art, to not deleteriously interfere with the resonant frequency of the ultrasonic horn 15.

Figure 2:
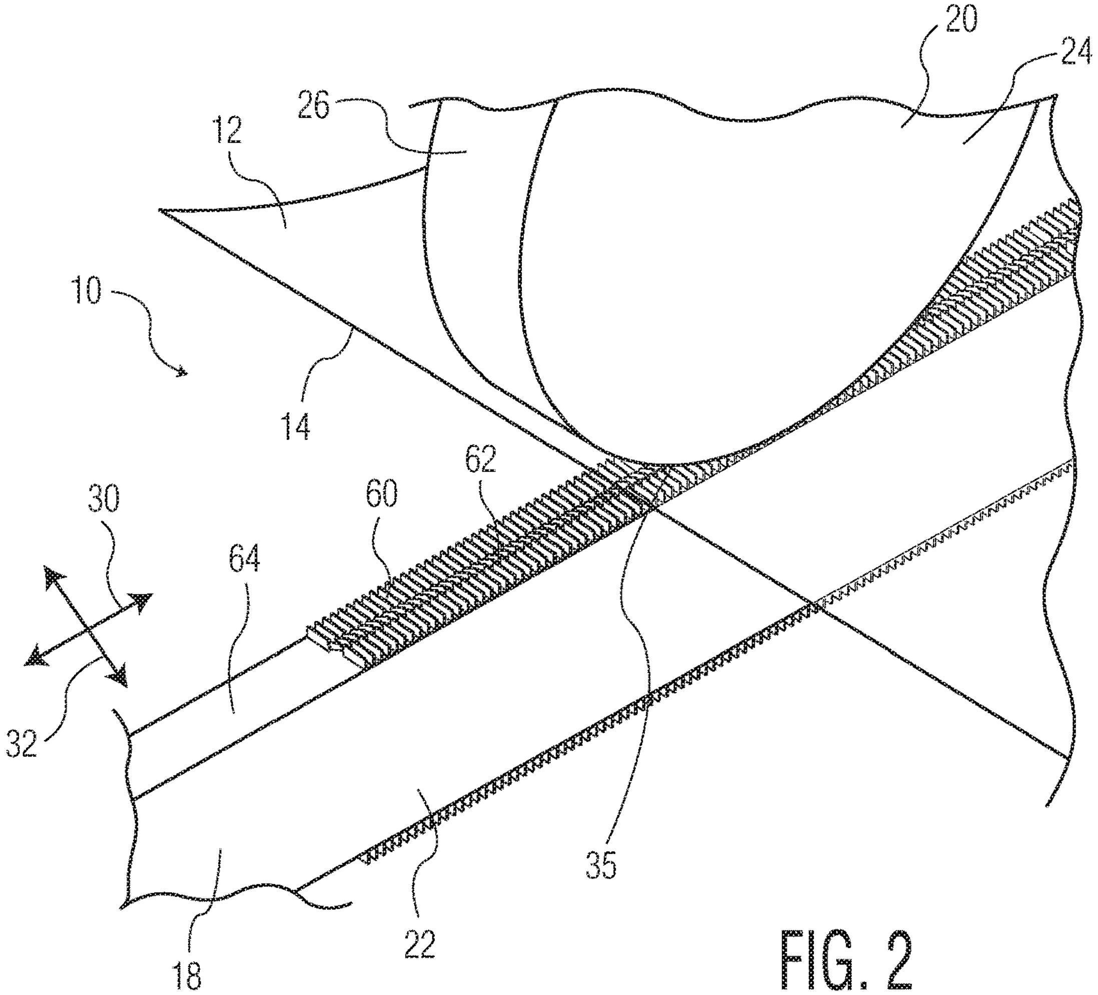
FIG. 2 is a close-up top, side perspective view of the exemplary embodiment of the ultrasonic bonding system from FIG. 1.

Referring back to FIGS. 1 and 2, the first energy application device 18 includes a primary bonding pattern 60 and a secondary bonding pattern 62. The primary bonding pattern 60 in combination with the secondary bonding pattern 62 extends continuously across the first energy application device 18 in the cross-machine direction 30. Desirably, during operation, the primary bonding pattern 60 provides non-continuous contact in the cross-machine direction 30 and the secondary bonding pattern 62 provides continuous contact in the cross-machine direction 30.

In one embodiment, as webs of material 12, 14 pass through the ultrasonic bonding system 10, energy is applied to the webs 12, 14 at locations on the webs corresponding to the respective protrusions or bonding elements 54, 56, thereby bonding the two web materials together to form a composite web. In another embodiment, as webs of material 12, 14 pass through the ultrasonic bonding system 10, energy is applied to the webs at locations on the webs corresponding to the respective protrusions 54 on the primary bonding pattern 60 only, thereby bonding the two web materials 12, 14 together to form a composite web 16. In this embodiment, the secondary bonding pattern 62 acts as a support for the ultrasonic horn 24 as it passes over the anvil 22 and webs of material 12, 14.

The primary bonding pattern 60 comprises a primary bonding area defined as the total area of one of the distal end surfaces of the primary bonding pattern elements 54. The secondary bonding pattern 62 comprises a second bonding area defined as the total area of one of the distal end surfaces of the secondary bonding pattern elements 56. Desirably, the primary bonding area is greater than the secondary bonding area. In desirable embodiments, the secondary bonding area is between about 10 and about 49 percent of the primary bonding area.

Figure 3:
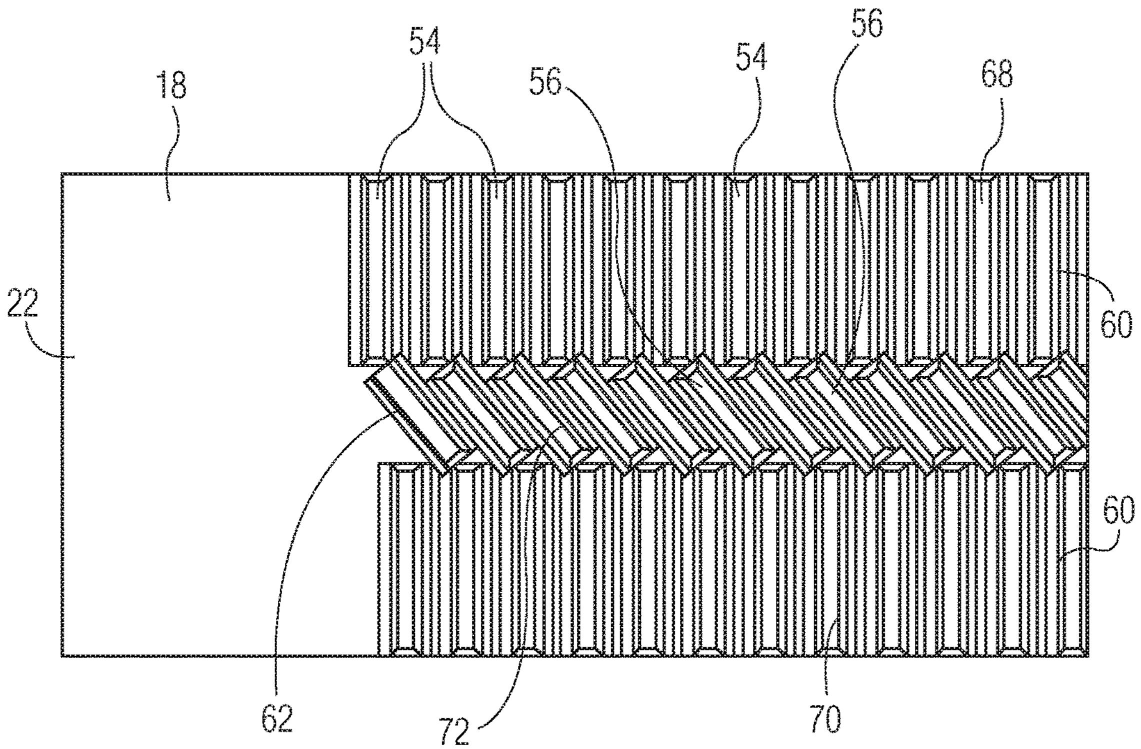
FIG. 3 is a top view of a pattern for use within the ultrasonic bonding system of FIG. 1.

FIG. 3 illustrates one desirable embodiment of an anvil 22 illustrating the primary bonding pattern 60 of raised bonding elements 54 and secondary bonding pattern 62 of raised bonding elements 56. The primary bonding pattern 60 comprises at least one row 68 of discreet bars extending in the machine direction 32. In this embodiment, the primary bonding pattern 60 comprises two rows 68, 70 of discreet bars extending in the machine direction 32 spaced apart in the cross-machine direction 30, both rows 68, 70 extending along both edges of the anvil 22. This primary bonding pattern 60 is configured to allow maximum neck-down and percent elongation of the composite material when the garment is strained perpendicular to the axis of the bond.

In this embodiment, the secondary bonding pattern 62 sits between the two rows 68, 70 of discreet bars within the primary bonding pattern 60 and comprises a row 72 of discreet bars extending in both the cross-machine 30 and machine direction 32.

The discreet bars of the secondary bonding pattern 62 are spaced apart, desirably providing that the secondary bonding pattern 62 is not continuous in the cross-machine direction 30 preventing severing of the composite 16 during bonding. This allows for further processing of the web 16 as it continues down the manufacturing line. It is important to note that the primary and secondary bonding patterns 60, 62 when combined extend the entire length of the energy path location 35 to ensure support of the ultrasonic horn 24 upon the anvil 22 during operation. In addition, while not continuous, angling of the discrete bars within the secondary bonding pattern 62 results in continuous contact during operation across the energy application path 35 as well to ensure support of the ultrasonic horn 24.

A significant benefit of supporting the ultrasonic horn 24 through operation is reduction of power feedback spikes in addition to better consistency of bonding strength. Feedback spikes occur as a result of characteristics of contact variation in conventional bond patterns between an anvil and a rotary ultrasonic horn. Conventional bond patterns tend to demonstrate a wide variation in composite contact lengths as compared to respective average composite contact lengths. A variation in composite contact lengths causes a corresponding, and typically proportional, variation in power distribution for a conventional bond pattern. Such variation is a result of e.g. bond patterns defining a rectangular arrangement of rows and lines, perpendicular to each other, of points extending along and perpendicularly across the length of the bond pattern. Thus, composite contact length of such conventional patterns varies for each transverse row of points from a maximum contact length when the row is in the nip, to zero, or something approaching zero, between rows, thereby developing corresponding power spike extremes at each row of points/dots/circles, whereby the effective diameter of such anvil roll varies slightly between successive transverse rows of points, and wherein each such variation contributes to vibration of the horn and anvil at the nip.

By combining primary and secondary bonding patterns 60, 62 extending the entire length of the energy path 35 operation of the bonding system ensures support of the ultrasonic horn 24 upon the anvil 22 during operation described herein reducing the power spikes, and creating more stability for the process. This lowers bond variability within the composite web, increasing elongation of the material and strength of the bonds.

Figure 4:
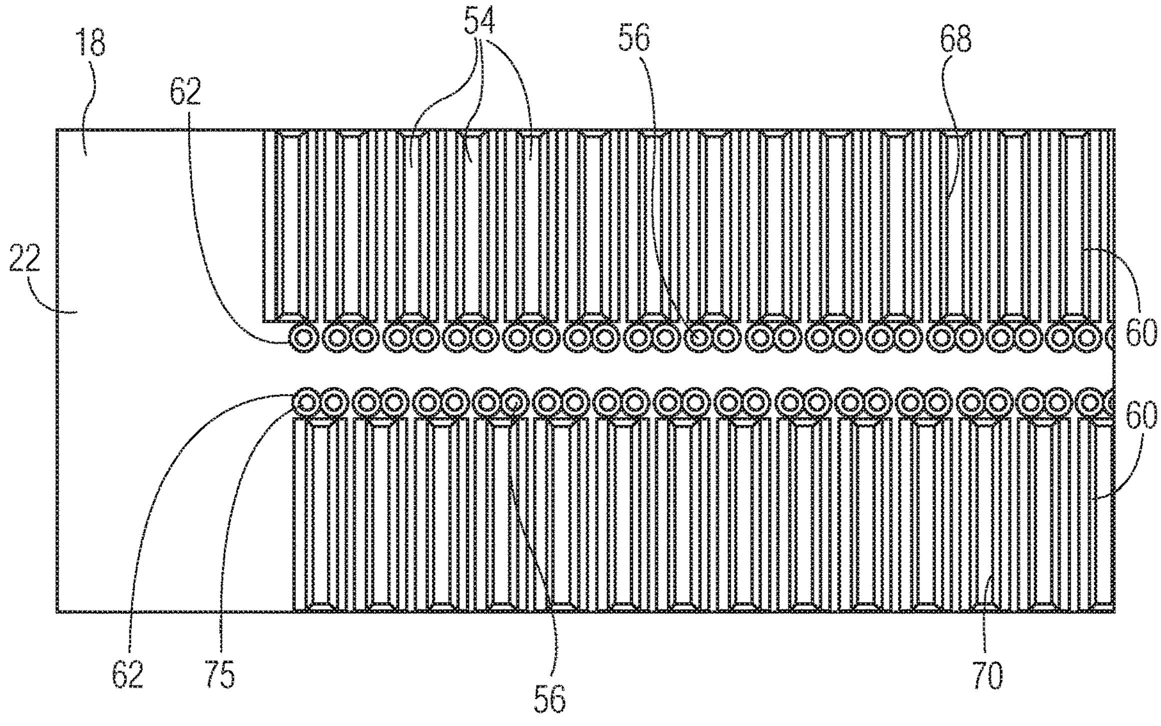
FIG. 4 is a top view of an alternative pattern for use within the ultrasonic bonding system of FIG. 1.

FIG. 4 illustrates another desirable embodiment of an anvil 22 illustrating the primary bonding pattern 60 of raised bonding elements 54 and secondary bonding pattern 62 of raised bonding elements 56. Similar to FIG. 3, the primary bonding pattern comprises two rows 68, 70 of discreet bars extending in the machine direction 32, the discreet bars spaced apart in the cross-machine direction 30. In this embodiment, the secondary bonding pattern 62 is placed between the two rows 68, 70 of discreet bars within the primary bonding pattern 60 and comprises at least one row 62 of discreet circular elements 75 extending in the cross-machine direction 30. The discreet bars of the secondary bonding pattern 62 are spaced apart, desirably providing that the secondary bonding pattern 62 is not continuous in the cross-machine direction 30 preventing severing of the composite during bonding. Similarly, the primary and secondary bonding patterns 60, 62 of this embodiment when combined to extend the entire length of the energy path location 35 to ensure support of the ultrasonic horn 24 upon the anvil 22 during operation.

Figure 5:
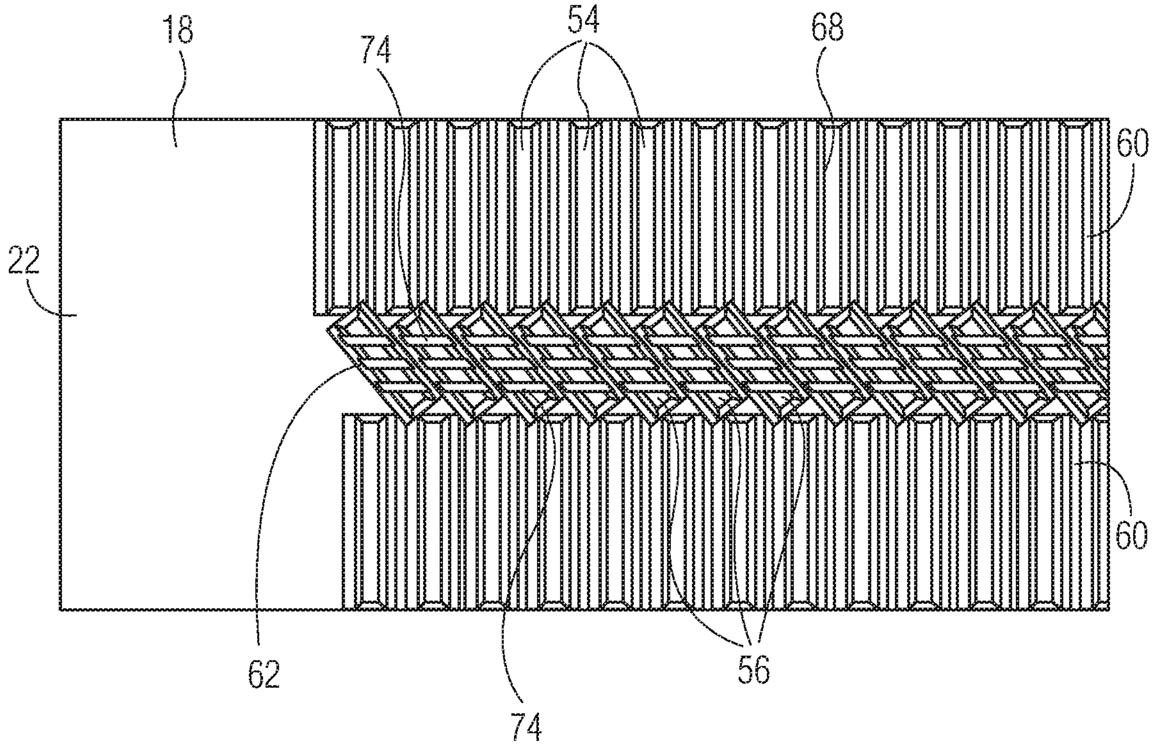
FIG. 5 is a top view of an alternative pattern for use within the ultrasonic bonding system of FIG. 1.

FIG. 5 illustrates another desirable embodiment of an anvil 22 illustrating the primary bonding pattern 60 of raised bonding elements 54 and secondary bonding pattern 62 of raised bonding elements 56. Similar to FIG. 3, the primary bonding pattern 60 comprises two rows 68, 70 of discreet bars extending in the machine direction 32, the discreet bars spaced apart in the cross-machine direction. In this embodiment, the secondary bonding pattern 62 is placed between the two rows 68, 70 of discreet bars within the primary bonding pattern 60 and comprises a row of discreet bars extending in both the cross-machine 30 and machine direction 32. In addition, the discreet bars of the secondary bonding pattern 62 may have gaps 74 formed within to provide that the secondary bonding pattern 62 is not continuous in the cross-machine direction 30 preventing severing of the composite during bonding.

Figure 6:
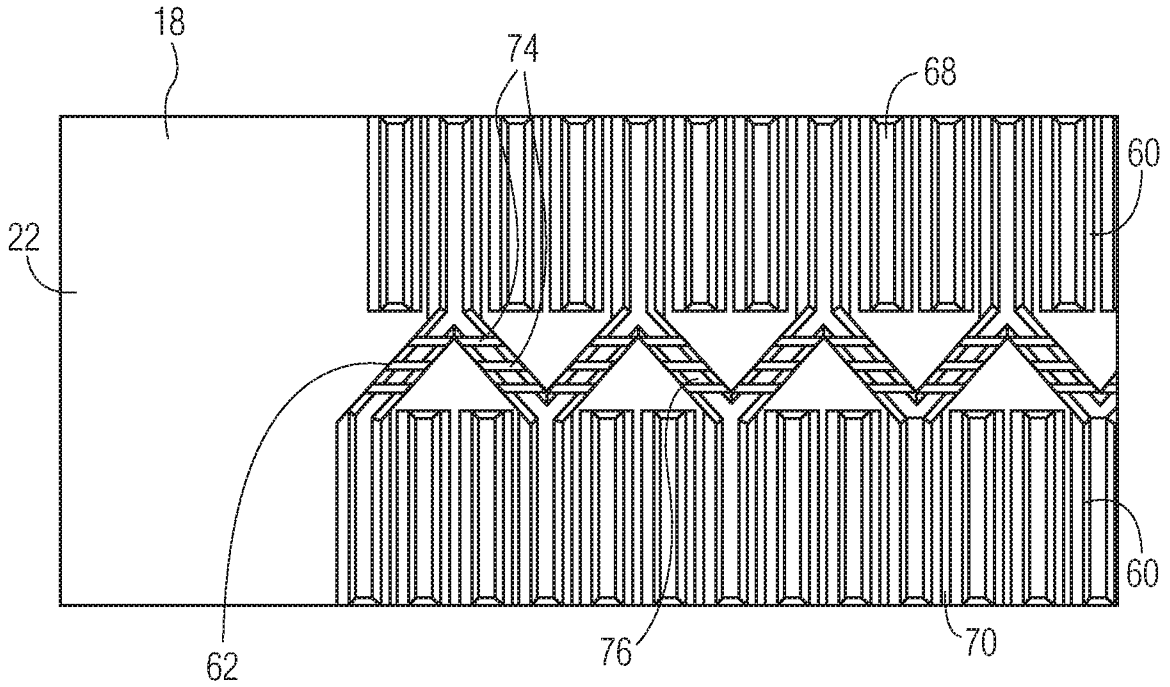
FIG. 6 is a top view of an alternative pattern for use within the ultrasonic bonding system of FIG. 1.

FIG. 6 illustrates another desirable embodiment of an anvil 22 illustrating the primary bonding pattern 60 of raised bonding elements 54 and secondary bonding pattern 62 of raised bonding elements 56. Similar to FIG. 3, the primary bonding pattern comprises two rows 68, 70 of discreet bars extending in the machine direction 32, the discreet bars spaced apart in the cross-machine direction. In this embodiment, the secondary bonding pattern 62 is placed between the two rows 68, 70 of discreet bars within the primary bonding pattern 60 and comprises a chevron pattern 76 of bars extending in both the cross-machine 30 and machine direction 32. In addition, the chevron pattern 76 of the secondary bonding pattern 62 may have gaps 74 formed within to provide that the secondary bonding pattern 62 is not continuous in the cross-machine direction 30 preventing severing of the composite during bonding.

Figure 7:
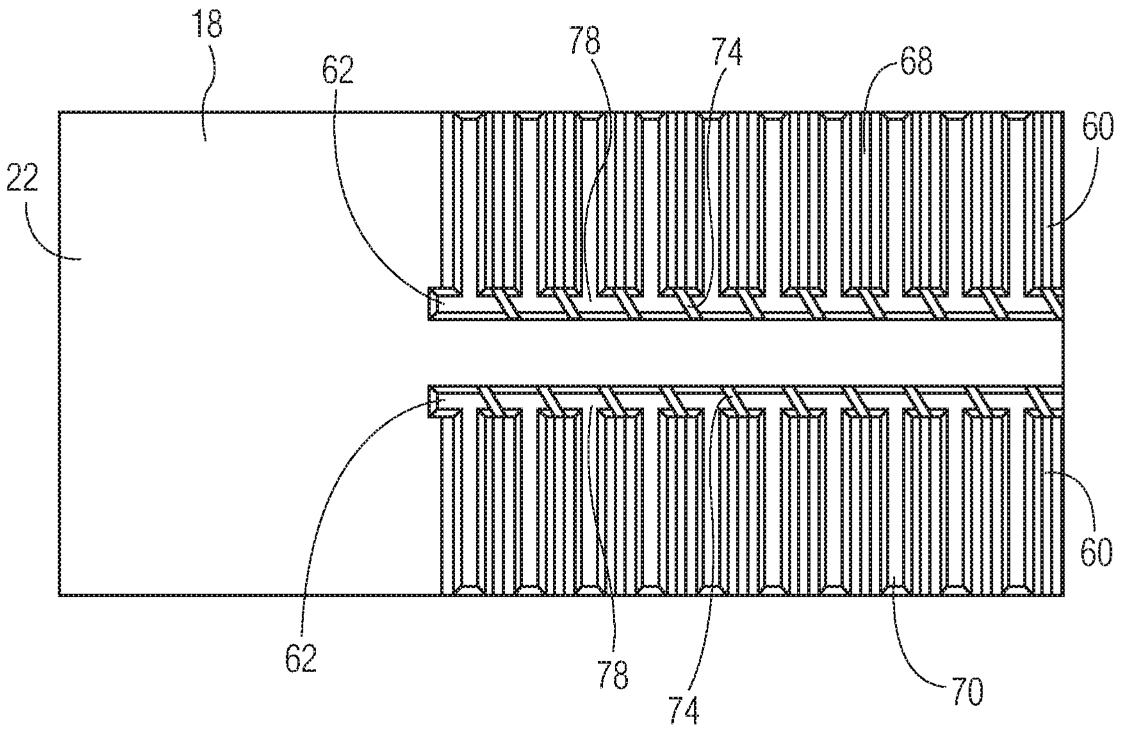
FIG. 7 is a top view of an alternative pattern for use within the ultrasonic bonding system of FIG. 1.

FIG. 7 illustrates another desirable embodiment of anvil 22 illustrating the primary bonding pattern 60 of raised bonding elements 54 and secondary bonding pattern 62 of raised bonding elements 56. Similar to FIG. 3, the primary bonding pattern 60 comprises two rows 68, 70 of discreet bars extending in the machine direction 32 spaced apart in the cross-machine direction. In this embodiment, the secondary bonding pattern 62 is placed between the two rows 68, 70 of discreet bars within the primary bonding pattern 60 and comprises a single row of material 78 extending in machine direction 32 adjacent the primary bonding pattern 60. In addition, the single row of material 78 of the secondary bonding pattern 62 may have gaps 74 formed within to provide that the secondary bonding pattern 62 is not continuous in the cross-machine direction 30 preventing severing of the composite during bonding. This design allows for the primary and secondary bonding patterns 60, 62 of this embodiment when combined to extend the entire length of the energy path location 35 to ensure support of the ultrasonic horn 24 upon the anvil during operation.

The patterns described within FIGS. 3-7 are meant for use with rotary ultrasonic systems like that described within U.S. Pat. No. 5,667,608 to Rajala et al., where the ultrasonic horn rolls along the anvil surface during operation as opposed to plunge type ultrasonic bonding where there is no relative motion between horn and anvil during bonding. The anvil patterns 60, 62 described here provide continuous support for the horn 24 as it rolls along the anvil 22 which minimizes both bond strength variability and generator overloading resulting in lower bond strength variability and greater productivity.

The ultrasonic bonding system 10 may be used to make disposable type garments such as diapers, training pants, feminine care products, incontinence garments, and the like. The ultrasonic bonding system may be used for production of disposable type garments in a continuous combined web, where the garment in the web extend transverse to the web, with the waist portions of the garments extending along the machine direction of the web, and the front and back portions of the garments being on opposing sides of the web. In the embodiments illustrated, the bonds join the first and second webs of material at locations generally corresponding to the ultimate locations of side seams in the finished garments.

Figure 8A:
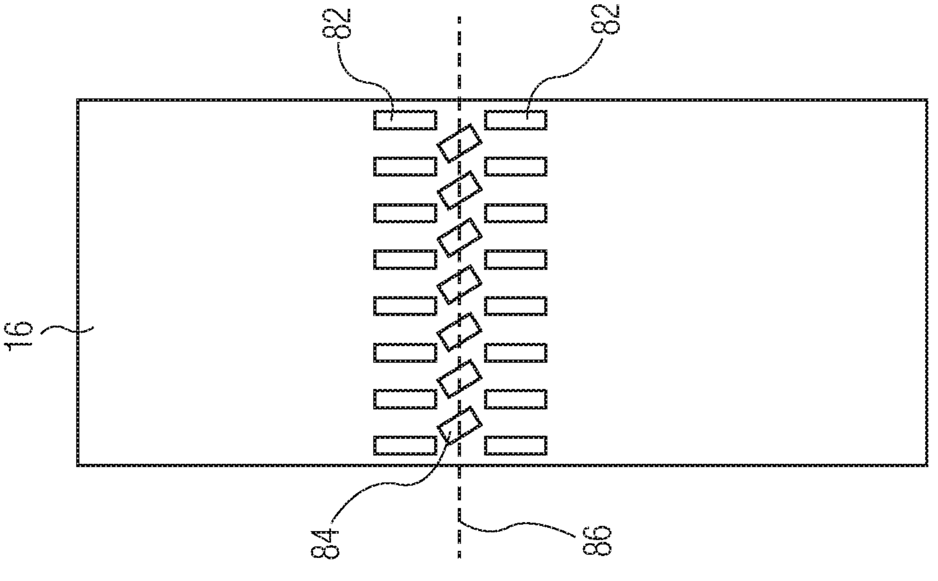
FIG. 8A illustrates an exemplary composite web manufactured utilizing the ultrasonic bonding system of FIG. 1 and the pattern for use of the system of FIG. 3.
Figure 8B:
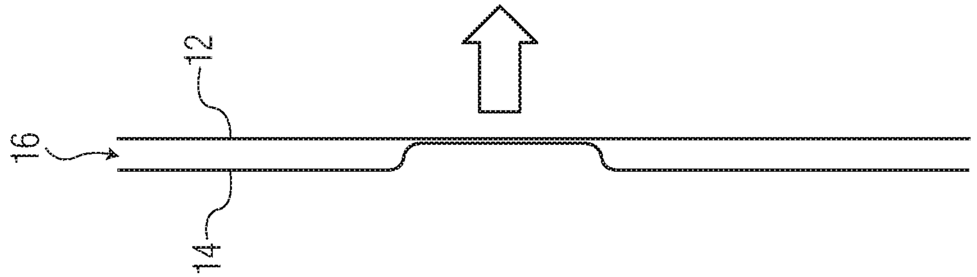
FIG. 8B illustrates a cross-sectional view of the composite web shown in FIG. 8A.
Figure 8C:
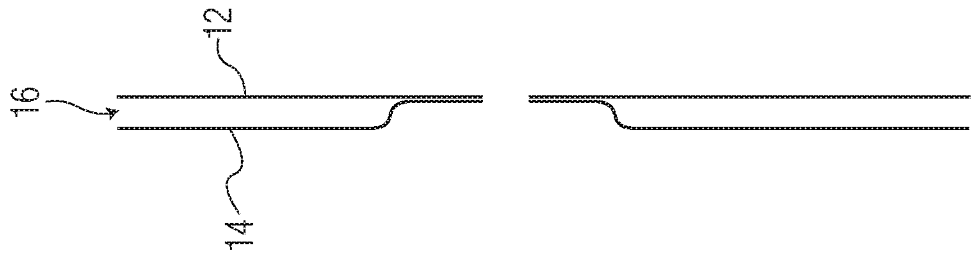
FIG. 8C illustrates a cross-sectional view of the composite web shown in FIG. 8A after cutting of the composite web.
Figure 8D:
FIG. 8D illustrates a cross-sectional view of the composite web shown in FIG. 8A.

As illustrated in FIGS. 8A-8D, a composite web 16 is formed by the ultrasonic bonding system 10 by combining a first web of material 12 and a second web of material 14 and utilizing the primary and secondary bonding patterns 60, 62 illustrated in FIG. 3. FIG. 8A illustrates a top view of the composite web 16 showing the resultant primary bond pattern 82 and secondary bond pattern 84 within the composite web 16. Since less than half of total bond energy was applied through the secondary bonding pattern, the secondary bond pattern 84 does not contribute to the side seam bond strength and does not inhibit the cross-machine direction neck-down of the garment material when the composite web 16 is strained perpendicular to the axis of the bond. FIGS. 8B and 8C illustrate a cross-sectional view of the composite material 16 before and after cutting the material between the primary bond patterns corresponding with the secondary bond pattern within the material at a cut line 86. Once cut, the composite web 16 is cut into two products 90, 92 and as illustrated is representative of a side panel of an absorbent article. The primary bond pattern 82 results in a flanged side seam 94 that has the bond strength required for use of the product 90, 92 by a consumer.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of bonding a first web of material to a second web of material to form a composite material, the method comprising the steps of:

(a) providing a first web of material and a second web of material moving in a machine direction;

(b) providing a first energy application device extending transverse in a cross-machine direction, the first energy application device including a primary bonding pattern and a secondary bonding pattern, wherein the primary bonding pattern in combination with the secondary bonding pattern extends continuously in the cross-machine direction;

(c) providing a second energy application device; and (d) moving the second energy application device in the cross-machine direction, and thereby extending the second energy application device over the first energy application device and operating the first and second energy application devices in combination and thereby applying energy to the first web of material and the second web of material at a line moving progressively across the first web of material and the second web of material to bond the first web of material to the second web of material.

2. The method of claim 1 wherein the first energy application device comprises an anvil and the second energy application device comprises a rotary ultrasonic horn.

3. The method of claim 1 wherein operating the first and second energy application devices in combination and thereby applying energy to the first web of material and the second web of material bonds only through the primary bonding pattern.

4. The method of claim 1 wherein the secondary bonding pattern provides support for the secondary energy application device when operating the first and second energy application devices in combination.

5. The method of claim 4 wherein the secondary bonding pattern does not provide energy to the first web of material and the second web of material.

6. The method of claim 1 wherein the secondary bonding pattern is non-continuous in the cross-machine direction.

7. The method of claim 1 wherein the primary bonding pattern comprises at least one row of discreet bars extending in the machine direction, wherein the discreet bars are spaced apart in the cross-machine direction, wherein the secondary boding pattern provides support where the discreet bars are spaced apart.

8. The method of claim 7 wherein the primary bonding pattern comprises two rows of discreet bars extending in the machine direction wherein the discreet bars are spaced apart in the cross-machine direction.

9. The method of claim 1 wherein the secondary bonding pattern comprises discreet bars extending at an angle to the machine direction.

10. The method of claim 1 wherein the secondary bonding pattern comprises a series of circular elements extending across the first energy application device in the cross-machine direction.

11. The method of claim 1 further comprising maintaining the web for further processing after bonding the first web of material to the second web of material.

12. The method of claim 1 wherein the primary bonding pattern comprises a primary bonding area, and the secondary bonding pattern comprises a secondary bonding area, wherein the secondary bonding area is between about 10 and about 49 percent of the primary bonding area.

13. The method of claim 1 further comprising applying pressure when operating the first and second energy application devices in combination.

14. A method of bonding a first web of material to a second web of material, the method comprising the steps of:

(a) providing a first web of material and a second web of material moving in a machine direction;

(b) providing a first energy application device extending transverse in a cross-machine direction, the first energy application device including a primary bonding pattern and a secondary bonding pattern;

(c) providing a second energy application device; and (d) moving the second energy application device in the cross-machine direction, and thereby extending the second energy application device over the first energy application device and operating the first and second energy application devices in combination and thereby applying energy to the first web of material and the second web of material at a line moving progressively across the first web of material and the second web of material to form a composite material, wherein the primary bonding pattern provides non-continuous contact between the first energy application device and the second energy application device in the cross-machine direction and the secondary bonding pattern provides continuous contact between the first energy application device and the second energy application device in the cross-machine direction.

15. The method of claim 14 wherein the first energy application device comprises an anvil and the second energy application device comprises a rotary ultrasonic horn.

16. The method of claim 14 wherein operating the first and second energy application devices in combination and thereby applying energy to the first web of material and the second web of material bonds only through the primary bonding pattern.

17. The method of claim 14 wherein the secondary bonding pattern provides support for the secondary energy application device when operating the first and second energy application devices in combination.

18. The method of claim 14 wherein the secondary bonding pattern does not provide energy to the first web of material and the second web of material.

19. The method of claim 14 wherein the secondary bonding pattern is non-continuous in the cross-machine direction.

20. The method of claim 14 wherein the primary bonding pattern comprises at least one row of discreet bars extending in the machine direction, wherein the discreet bars are spaced apart in the cross-machine direction, wherein the secondary boding pattern provides support where the discreet bars are spaced apart.

21. The method of claim 20 wherein the primary bonding pattern comprises two rows of discreet bars extending in the machine direction wherein the discreet bars are spaced apart in the cross-machine direction.

22. The method of claim 14 wherein the secondary bonding pattern comprises discreet bars extending at an angle to the machine direction.

23. The method of claim 14 wherein the secondary bonding pattern comprises a series of circular elements extending across the first energy application device in the cross-machine direction.

24. The method of claim 14 further comprising maintaining the web for further processing after bonding the first web of material to the second web of material.

25. The method of claim 14 wherein the primary bonding pattern comprises a primary bonding area, and the secondary bonding pattern comprises a secondary bonding area, wherein the secondary bonding area is between about 10 and about 49 percent of the primary bonding area.

26. The method of claim 14 further comprising applying pressure when operating the first and second energy application devices in combination.

* * * * *